United States Patent [19]
Mee et al.

[11] Patent Number: 5,825,501
[45] Date of Patent: Oct. 20, 1998

[54] STRUCTURE AND YARN SENSOR FOR FABRIC

[75] Inventors: David K. Mee, Knoxville; Glenn O. Allgood, Powell; Larry R. Mooney, Knoxville; Michael G. Duncan; John C. Turner, both of Clinton; Dale A. Treece, Knoxville, all of Tenn.

[73] Assignee: Lockheed Martin Energy Systems, Inc., Oak Ridge, Tenn.

[21] Appl. No.: 818,157

[22] Filed: Mar. 14, 1997

[51] Int. Cl.⁶ .................................................. G01N 21/84
[52] U.S. Cl. ............................................. 356/429; 356/430
[58] Field of Search ................................... 356/429–431, 356/238, 239, 420, 394; 250/559.42, 559.12–559.15, 559.39, 559.37, 559.47

[56] References Cited

U.S. PATENT DOCUMENTS

| | | | |
|---|---|---|---|
| 3,729,635 | 4/1973 | Shottenfeld et al. | 250/219 S |
| 3,746,865 | 7/1973 | Burch | 250/219 S |
| 3,757,211 | 9/1973 | Goto | 324/61 R |
| 3,786,265 | 1/1974 | Abilock et al. | 250/219 DF |
| 4,103,177 | 7/1978 | Sanford et al. | 250/562 |
| 4,384,596 | 5/1983 | Brouwer et al. | 139/370.2 |
| 4,643,230 | 2/1987 | Aemmer et al. | 139/1 B |
| 5,221,960 | 6/1993 | Akerlind et al. | 356/429 |
| 5,541,734 | 7/1996 | Nevel et al. | 356/385 |
| 5,570,188 | 10/1996 | Nevel et al. | 356/385 |
| 5,615,014 | 3/1997 | Okuda | 356/429 |
| 5,694,979 | 12/1997 | Toda | 139/1 B |
| 5,703,688 | 12/1997 | Bell | 356/430 |

*Primary Examiner*—Frank G. Font
*Assistant Examiner*—Michael F. Stafira
*Attorney, Agent, or Firm*—J. Kenneth Davis

[57] ABSTRACT

A structure and yarn sensor for fabric directly determines pick density in a fabric thereby allowing fabric length and velocity to be calculated from a count of the picks made by the sensor over known time intervals. The structure and yarn sensor is also capable of detecting full length woven defects and fabric. As a result, an inexpensive on-line pick (or course) density measurement can be performed which allows a loom or knitting machine to be adjusted by either manual or automatic means to maintain closer fiber density tolerances. Such a sensor apparatus dramatically reduces fabric production costs and significantly improves fabric consistency and quality for woven or knitted fabric.

45 Claims, 13 Drawing Sheets

| Sequence # | Roll ID | Length | Picks | Amplitude | Width | Defect |
|---|---|---|---|---|---|---|
| 354028 | 11 | 413 | 19353 | 2.73E−01 | 4.98E+01 | NT |
| 355022 | 11 | 553 | 25927 | 0.00E+00 | 0.00E+00 | NT |
| 355219 | 11 | 578 | 27115 | −2.30E−02 | 0.00E+00 | NT |
| 355327 | 11 | 593 | 27810 | 1.35E+00 | 4.56E+01 | HH |
| 355564 | 11 | 620 | 29122 | 2.57E−01 | 4.07E+01 | H |
| 355686 | 11 | 635 | 29807 | −2.08E−01 | 3.91E+01 | NT |
| 355808 | 11 | 648 | 30423 | −2.01E+00 | 4.35E+01 | LL |
| 355993 | 11 | 674 | 31606 | −1.90E−00 | 5.68E+01 | LN |
| 356144 | 11 | 689 | 32310 | 5.09E−03 | 2.70E+01 | NT |
| 356296 | 11 | 705 | 33085 | 9.59E−01 | 3.86E+01 | WT1 |
| 356350 | 11 | 713 | 33446 | −7.72E−01 | 7.30E+01 | WT1 |
| 356454 | 11 | 722 | 33846 | −8.62E−02 | 7.30E+01 | WT1 |
| 356558 | 11 | 736 | 34535 | −1.11E−00 | 4.22E+01 | WT2 |
| 356621 | 11 | 745 | 34947 | 1.63E−00 | 4.91E+01 | WT2 |
| 356959 | 11 | 787 | 36938 | 0.00E+00 | 0.00E+00 | DP |
| 357027 | 11 | 793 | 37212 | −7.40E−02 | 4.07E+01 | NT |
| 357196 | 11 | 803 | 37702 | 1.61E−01 | 4.00E+01 | DP |
| 357546 | 11 | 853 | 40020 | −3.93E−01 | 4.32E+01 | MP |
| 358149 | 11 | 937 | 43692 | 1.40E−01 | 4.27E+01 | EO |
| 358226 | 11 | 948 | 44471 | 1.46E−01 | 4.34E+01 | EI |
| 358415 | 11 | 974 | 45727 | 1.78E−02 | 2.76E+01 | DE |
| 358553 | 11 | 994 | 46644 | 9.50E−01 | 5.00E+01 | MFS |
| 358738 | 11 | 1019 | 47856 | −3.69E−01 | 3.82E+01 | MFE |

FIG. 10

STRUCTURE AND YARN SENSOR FOR FABRIC

The United States Government has rights in this invention pursuant to Contract No. DE-AC05-84OR21400 between the United States Department of Energy and Lockheed Martin Energy Systems, Inc. The invention arose within work done under CRADA No. ORNL 94-0253.

FIELD OF THE INVENTION

The present invention relates to methods and apparatus for ensuring the quality and yarn density in textile fabrics or cloth, both woven and knitted, and more particularly to methods and apparatus for continuous, in-process monitoring the number of filling yarns per unit length, commonly referred to as picks per inch in woven fabrics, and the number of courses per inch in knitted fabrics.

BACKGROUND OF THE INVENTION

In the weaving of fabrics, one of the most important specifications is the number of filling yarns per unit length, commonly called picks per inch. The costs of manufacturing fabrics increase significantly as the number of picks per inch increases. This important parameter is measured to ensure that the specified pick density is being achieved. Typically manufacturers of woven goods measure this parameter visually, using a magnifying "pick glass". Alternative approaches which calculate pick density indirectly from detections of cloth movement and machine speed have been the source of problems, and improved methods and apparatus have long been desired.

It is necessary to allow some margin of error in pick density to prevent producing significant quantities of cloth which do not meet manufacturing specifications. This margin of error and its associated costs must be balanced against the risk of having to sell at significantly lower prices if the cloth does not meet the pick density specification. An inexpensive on-loom pick density measurement method would allow the loom to be adjusted, either manually or automatically, to maintain closer pick density tolerances and save both time and money.

Thus, implementation of an inexpensive on-loom pick density measurement has long been sought to allow rapid adjustment of the loom by either manual or automatic means to maintain closer pick density tolerances. Such a measurement and subsequent compensation scheme would dramatically reduce fabric production costs and significantly improve fabric consistency and quality.

Detecting defects in fabric as it is manufactured and processed is also important. Fabric defects, commonly known to the skilled artisan, can include double picks, missed picks, heavy yarn, light yarn, slubs, holes, drop stitches, needle runs and double yarn.

It is also desired that maps be provided to indicate the position of such defects. Maps may be used for grading rolls of cloth, communicating defect locations to customers, cutting out defective pieces of cloth, positioning fabric on cutting tables, and identifying causes of defects.

When cloth is unrolled for cutting on cutting tables or for inspection, the pick (or in the case of knitted fabrics, course) density can change based on environmental conditions and tension on the cloth. If such maps assume constant pick (or course) density in downstream processes, this shrinking or stretching may introduce errors in the locating of defects in the map and may thus affect adjustment of cutting templates or automatic registration of a defect in the center of an inspection frame. Preventing errors in a fabric map, such as defect location errors, may require scaling the location of fabric defects based on the ratio of the densities at the initial inspection and at the later processing step. It is thus desirable to perform a yarn density measurement at two locations, the point of inspection and at the subsequent process of interest, such that compensation may be made.

OBJECTS OF THE INVENTION

Accordingly, it is an object of the present invention to provide a new and improved structure and yarn sensor with capability for detecting yarn density, yarn density gradient, pick (or course) count, fabric velocity, and fabric length.

It is another object of the present invention to provide a method for detecting fabric defects and defect site locations for generation of a defect map.

Further and other objects of the present invention will become apparent from the description contained herein.

SUMMARY OF THE INVENTION

In accordance with one aspect of the present invention, a new and improved structure and yarn sensor apparatus for use with a fabric made with a plurality of yarns moving in a direction of travel, the fabric having a front side and a back side, the yarns being disposed generally across the width of the fabric, comprises: a light source directed so that light impinges upon a side of the fabric in a path of light propagation; a focusing lens disposed in the path of light propagation to focus the light; a cylindrical lens disposed in the path of light propagation to allow selective imaging of yarn in one dimension to be imaged on an array; an array comprising photodetectors, the array having a face, the photodetectors being disposed so that the focused light from the focusing lens impinges upon the face of the array of photodetectors to produce a scan, wherein the face is divided into a multiplicity of pixels, the array of photodetectors producing an output signal based on the fabric moving in the direction of travel during the scan; a timing control means producing a velocity gate signal, clock signals, a read signal, and a scan start signal, wherein the clock signal and the scan start signal are coupled to the array of photodetectors; a smoothing filter means coupled to the output of the array of photodetectors; a bias detection means coupled to the output of the array of photodetectors; a discriminator means having a positive input and a negative input, wherein one input is coupled to the output of the smoothing filter means and the other input is coupled to the output of the bias detection means; a pick selection and counting means having an input port, a reset port, and clock signal input ports, wherein the input port is coupled to the output of the discriminator port, the reset port is coupled to the scan start signal, and the clock inputs are coupled to the timing control clock signals, and wherein the scan pick selection and counting means determines which picks imaged on the face of the photodetectors during a scan will be used in the density calculation, provides a gated pixels signal during a scan while picks are being counted, provides a pick detected signal during a scan each time an additional pick is counted, and outputs a collected count of picks over multiple scans; a pixel selection and counting means having a reset port, an input port, clock signal input ports, and a pick detected input port, wherein the reset port is coupled to the scan start signal, the input port is coupled to the gated pixels signal, the clock inputs are coupled to the timing control clock signals, and the pick detected input port is coupled to the pick detected output, and wherein the pixel selection and counting means counts pixels during scans corresponding to the count of picks and outputs a collected count of pixels over multiple scans; an incremental pick density calculation means having inputs coupled to the read signal, the scan pick selection and counting output and the pixel selection and counting output, wherein the pick density calculation means produces an incremental pick density signal based on the pick count and the pixel count, wherein the pick density signal is representative of the density of picks in the fabric object imaged on the face of the array of photodetectors, and wherein the incremental pick density processor means resets scan pick selection and counting and pixel selection and counting means after performing a read.

In accordance with a second aspect of the present invention, A method for determining a yarn density in a fabric made with a plurality of yarns, the fabric having a front side and a back side, and having yarns which are disposed generally across the width of the fabric, which comprises the steps of: moving the fabric in a direction of travel; directing a light source so that light impinges upon the fabric in a path of light propagation; focusing the light so that the light impinges upon an array of photodetectors, wherein the array of photodetectors has a face which is divided into a multiplicity of pixels, whereby a number of yarns in a single direction in the fabric is imaged on a number of pixels in the face of the array of photodetectors to produce a scan; operating the array of photodetectors during a scan to produce an output signal which is based on the fabric moving in the direction of travel during the scan; counting the number of selected yarns in the fabric imaged on the face of the array of photodetectors during the scan; counting the number of pixels in the face of the array of photodetectors on which the number of selected yarns in the fabric is imaged during the scan; and determining the yarn density based on the number of yarns and the number of pixels.

In accordance with a third aspect of the present invention, a method for detecting defects and patterns in a fabric made with a plurality of yarns, the fabric having a front side and a back side, and having yarns which are disposed generally across the width of the fabric, comprises the steps of: moving the fabric in a direction of travel; directing a light source so that light impinges upon the fabric in a path of light propagation; focusing the light so that the light impinges upon an array of photodetectors, wherein the array of photodetectors has a face which is divided into a multiplicity of pixels, whereby a number of yarns in a single direction in the fabric are imaged on a number of pixels in the face of the array of photodetectors to produce a scan; operating the array of photodetectors during a scan to produce an output signal based on the fabric moving in the direction of travel during the scan; obtaining a signal, based on the output signal from the array of photodetectors; and determining defects and patterns in the fabric based on the signal from the array of photodetectors.

Other objects, advantages, and salient features will be more apparent when considered with the following detailed description and drawings that are provided to facilitate the understanding of the invention without any limitation thereto.

BRIEF DESCRIPTION OF THE DRAWINGS

FIG. 10 is a completed defect map, describing defects, locations, and classifications.

DETAILED DESCRIPTION OF THE INVENTION

General Description

Figure 1:
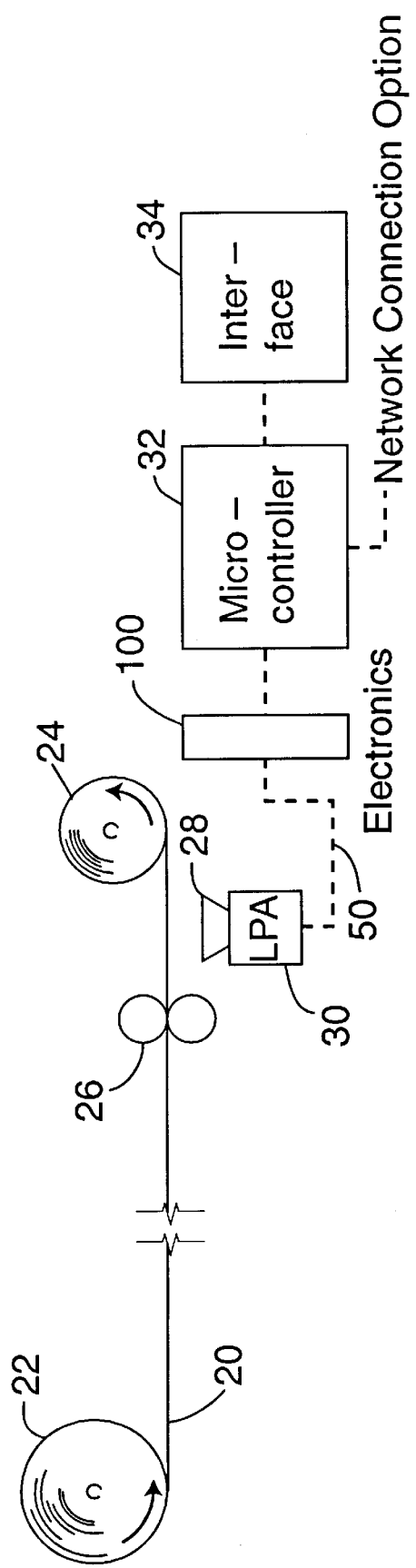
FIG. 1 is a schematic view of a structure and yarn sensor apparatus disposed in confronting relationship with fabric moving in a fabrication line.

For a better understanding of the invention, together with other and further objects, advantages, and capabilities thereof, reference is made to the following disclosure and the figures of the drawing, where like reference characters designate like or similar elements.

Referring to FIG. 1, fabric cloth 20 unrolled from a roll of fabric 22 can be advanced directly through a path in a textile mill. The cloth 20 is unrolled, for example, to be cut on a cutting table or for inspection. The device also functions well for on-line inspection during manufacturing operations. Portions of the path of the moving fabric in the textile mill are not shown in FIG. 1. During travel in the path the fabric 20 will, in some cases, shrink or stretch due to environmental conditions and tension on the cloth 20.

The density of yarn throughout the fabric 20 will often be non-uniform and vary in response to such stretching and shrinking or other nonuniformities caused during the manufacture of the fabric. At some point in the path the fabric 20 will often be collected onto a take-up roll 24 where it can be conveniently stored for further processing. Positioning rollers 26 can be disposed in the path to guide the fabric 20 to the take-up roll 24. The structure and yarn sensor apparatus is disposed in the path between the initial roll 22 and the take-up roll 24 according to the principles of the invention to measure the density of yarn in the fabric 20 moving in the path from the initial roll 22 to be wound around the take-up roll 24. The structure and yarn sensor should be positioned at the to point in the process where fabric density is desired (i.e. near the loom or take-up roll if the roll's pick density is the key parameter). The structure and yarn sensor has been demonstrated in on-loom applications. FIG. 1 is not intended to limit the scope of applications but rather to provide a general usage.

The structure and yarn sensor apparatus is disposed along the path of the moving fabric 20, in confronting relationship with one side of the moving fabric 20. The structure and yarn sensor apparatus comprises a light source 27 and a combination of lenses 28 and 201 to image picks in the fabric onto the face of the linear photodetector array 30. The linear photodetector array 30 is preferably embodied as a linear photodiode array (linear diode array). A linear phototransistor array may also be used to embody the linear photodetector array. The spatial information detected by the linear diode array enables detection of pick density in the moving fabric 20 using, for example, processing electronics 100 and a microprocessor 32. Other embodiments are possible depending on the speed of the application. Once the pick density is determined, fabric length and fabric velocity is calculated from a continuous count of the picks over specified time intervals. Certain full-length defects in the fill direction are identified with appropriate advanced signal processing. Setup parameters which customize the structure and yarn measurement to a particular fabric style are selected by a user with an interface device 34, which may include, for example, a keyboard and a display or a controller. The structure and yarn sensor apparatus can also be programmed and/or interrogated through a network for large factory installations. The structure and yarn sensor apparatus may be used for both woven or knitted fabric.

Optics

Figure 2:
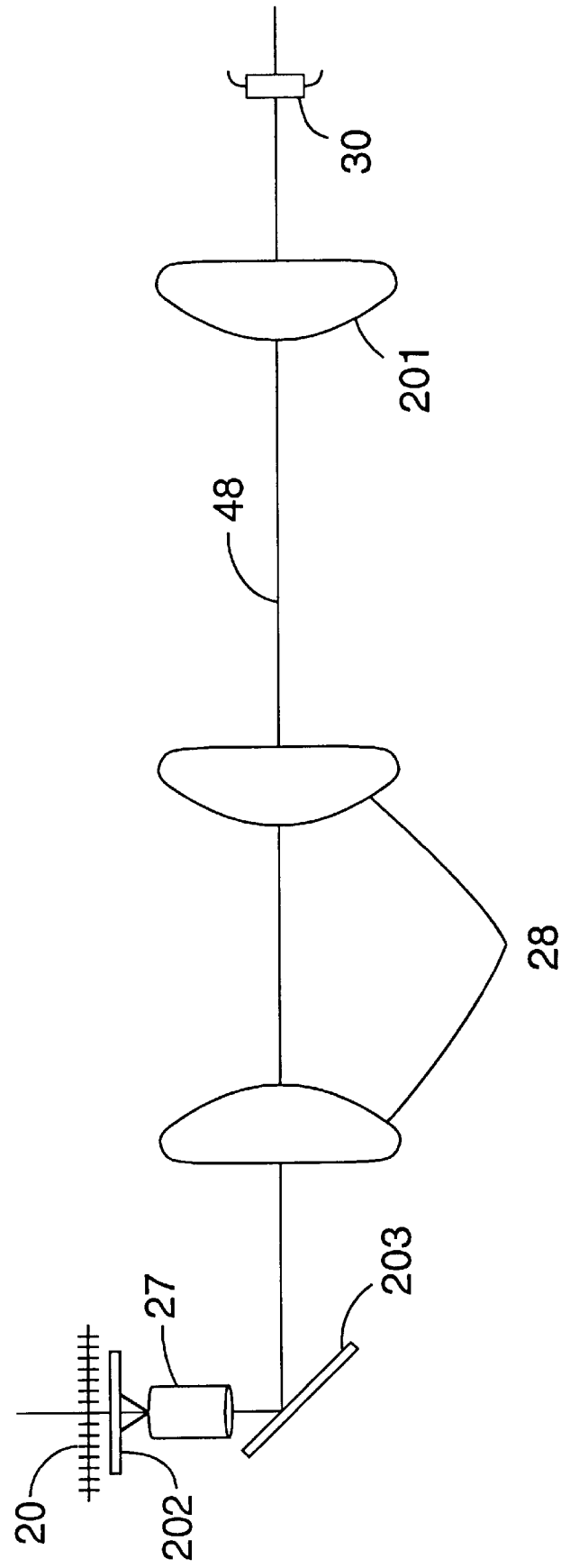
FIG. 2 is a schematic view of the optics in the structure and yarn sensor apparatus depicted in FIG. 1.

A fabric web 20 advances on an inspection frame or manufacturing process as shown in FIG. 1. The fabric comprises pick yarn oriented roughly parallel to the axis of the optics 28 and 201, as shown in FIG. 2. Movement of the fabric is in a direction in or out of the drawing page. In one embodiment, the yarn measurement device contacts the full width of the fabric in a direction perpendicular to the direction of movement to prevent creasing the fabric. The fabric is viewed through a window 202 in the side of the housing. The yarn measurement device is preferably enclosed in a housing which may comprise a tube with a flat milled on the side which contacts the cloth. The external surface of the window 202 may be flush with the flat on the housing.

The yarn measurement device includes a light source 27 which can preferably be enclosed in the yarn measurement device housing which is disposed on what is herein referred to as the front side of the fabric or located separately on the opposite side of the fabric (herein referred to as the back side), depending on the needs of particular applications. In the case where the light source 27 is contained in the device housing, the fabric may be illuminated from a shallow angle to the face of the fabric. This arrangement prevents the light source 27 from interfering with the image rays and also improves contrast since each pick casts a shadow.

In one embodiment, a front surface mirror 203 reflects the image of the fabric down a tube housing along the axis of light propagation 48. This arrangement allows the optics to be arranged in a desirable location. At least one non-astigmatic lens 28 (preferably achromat) located on axis 48 image the fabric onto the face of the linear diode array 30. An astigmatic lens 201, also located on axis 48, de-focuses warp yarn (yarn roughly perpendicular to pick yarn) which would otherwise interfere with the detection of picks. Thus, only the picks are in focus at the sensor array with the image appearing as a series of lines perpendicular to the sensor's line of photodetectors. Another alternative embodiment uses one or more cylindrical lenses to directly image only picks onto the array face.

Pick Density

The linear array of photodetectors 30 is preferably embodied as a linear photodiode array, i.e., a linear diode array. The linear diode array 30 is disposed at the focal point of the lens combination 28 in the path of light propagation 46. The face of the linear diode array 30 is divided into a number of diode elements, i.e., pixels which each measure a portion of the image focused on the face.

Figure 3:
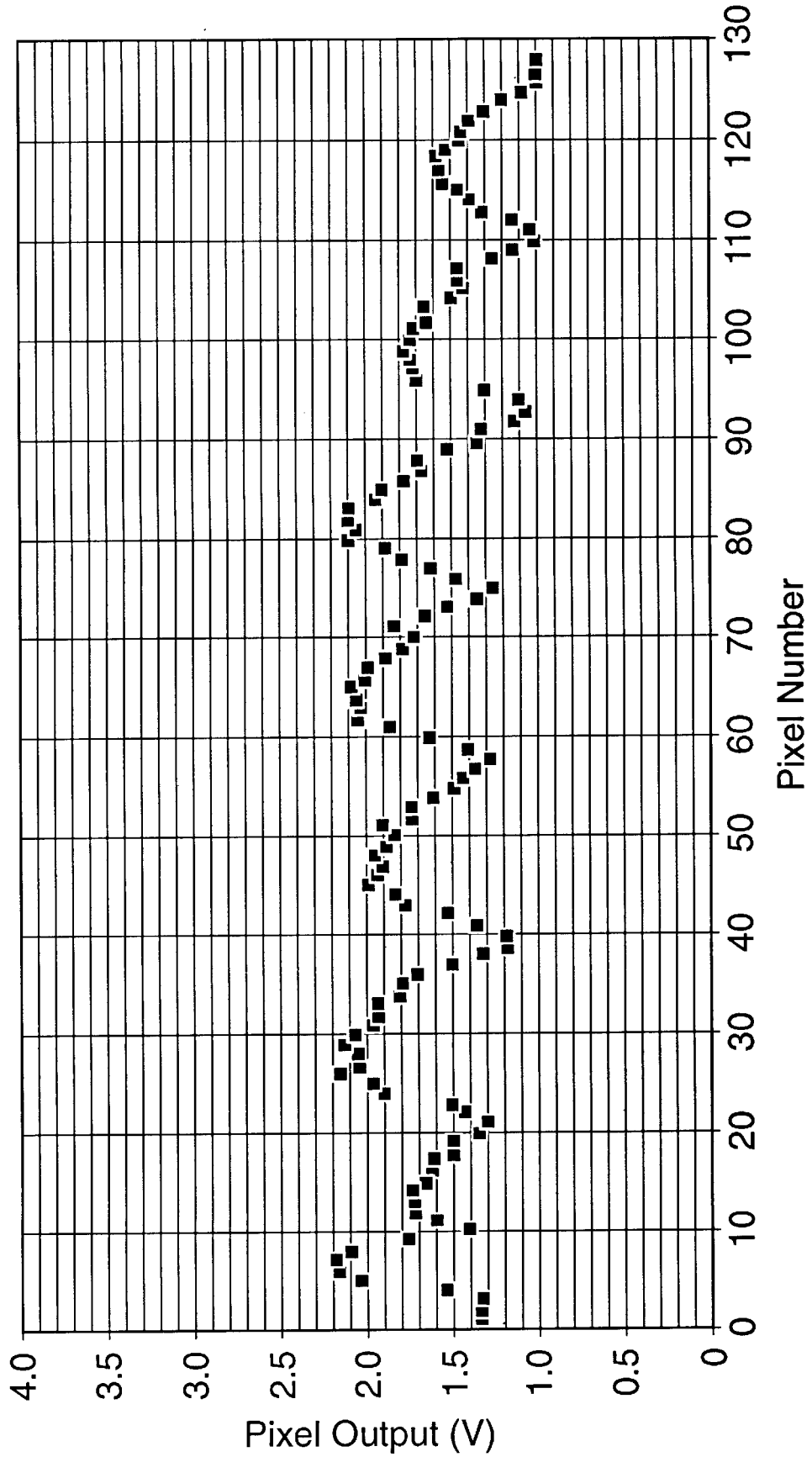
FIG. 3 is a plot of a scan of good woven fabric with front illumination showing a pick pattern therein.

The linear diode array 30 outputs a signal 50, as shown in FIG. 1. The output signal 50 can be a parallel or serial signal depending on speed requirements of the application. The signal 50 output from the linear diode array 30 may be processed in real-time to obtain spatial information representative of the fabric 20 as the fabric moves past the sensor. The image focused on the linear diode array 30 appears as a set of parallel lines, each representing, for example, one pick (i.e., one filling yarn) in the fabric 20. Picks on the array face appear as bright spots for applications using illumination from the detector housing. For embodiments wherein the fabric is back-lit, picks appear as dark regions on the array. With the appropriate magnification provided by the lenses 28, each pick falls on a number of linear diode array elements, i.e., a number of pixels, as shown in FIG. 3. FIG. 3 illustrates a scan of good woven fabric showing a pick pattern therein, where the fabric was illuminated from a bright source inside the detector housing.

The pick density of the fabric can be obtained from a count of specific picks and pixels from individual scans of the array's output. The averaged incremental pick density $\rho_k$ from k scans is:

$$\rho_k = \frac{\sum_{i=1}^{k} n_p(i)}{\delta \cdot \sum_{i=1}^{k} n_x(i)} \quad (1)$$

where $n_p(i)$ is the number of whole picks inside a selected window during scan i, $n_x(i)$ is the number of pixels over which these picks fall during scan i, and $\delta$ is a constant denoting the effective incremental distance represented by each array pixel. The "selected window" indicated above is set to exclude the following:

(1) The initial portion of the array where filters 60 and 62 have not charged sufficiently, (2) The array set-up pulse which does not contain valid data, and (3) Partial picks at the beginning and end of a scan which would cause error if included.

Figure 4:
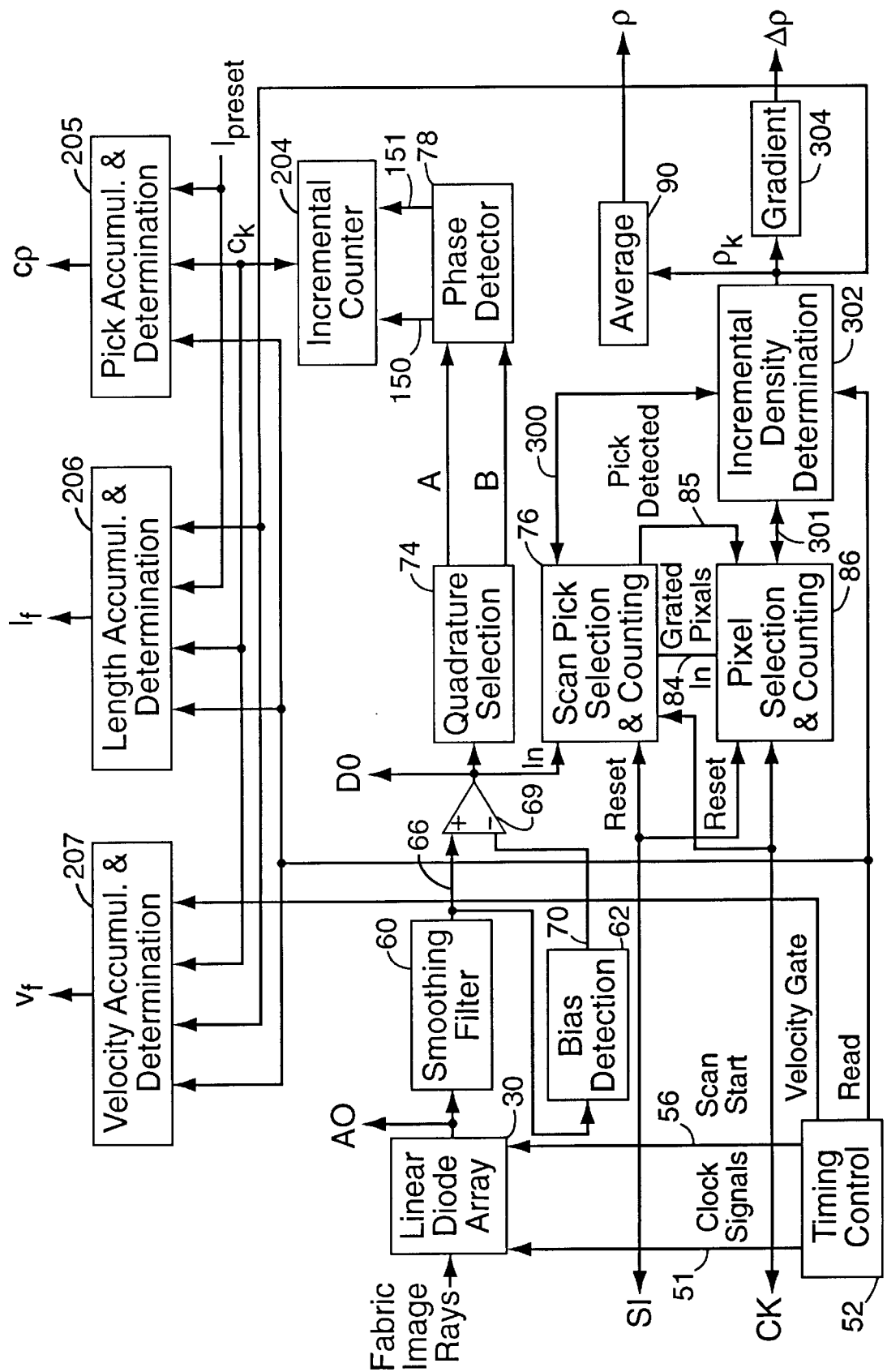
FIG. 4 is a schematic view of controller circuitry in the structure and yarn sensor apparatus shown in FIG. 1.

An embodiment is described below which utilizes the incremental pick density calculation above. The pick pattern imaged onto the face of the linear diode array 30 causes a series of voltage levels to be output from the array as shown in FIG. 3. Referring to FIG. 4, the linear diode array output AO, is filtered by smoothing filter 60 to eliminate discrepancies between pixel voltage levels and to smooth the stair step type signal. The smoothing filter 60 is embodied as a two pole filter with Q of about 1. The cut frequency of this filter is as close as possible to the signal's primary frequency without causing significant reduction in signal amplitude. A higher order low pass filter can be used as needed to meet the needs of more demanding applications. The smoothing filter output 66 is further filtered by bias detection circuit 62. The bias detection is typically embodied as a single pole filter, however, other embodiments can use other type filters or a fast processor to calculate the median of local maxima and minima. If a range of cloth is expected in the application, the cut frequencies of filters used in blocks 60 and 62 may be made adjustable.

The smoothing filter output 66 and the bias detection output 70 are compared by comparator 69. The output of the comparator DO is a discrete signal where pulses represent individual picks in the array scan. In this embodiment, the linear diode array 30 scans continuously causing DO to repeat scan information taken at slightly different times. Converting the analog output AO to a discrete signal DO before processing the data enables rapid analysis at a fraction of the cost of alternative schemes such as fast analog-to-digital converters and high speed processors.

The scan pick selection and counting section 76 selects which picks will be used in the incremental pick density calculation and counts them. Logic in this block provides the windowing function described immediately following Eq. 1. The intent of this window is to eliminate consideration of picks while filters in blocks 60 and 62 are charging at the first of a scan, to prevent use of the array set-up pixel which does not contain valid data, and to eliminate partial picks. In this embodiment, the window opens at the first trailing edge of a pick after the 24th clock cycle and closes on the last trailing edge before the 129th clock cycle. A counter in section 76 increments $n_p$ (i) at the trailing edge of each pick which occurs inside the scan window. One pick is removed from each scan's count since the first trailing edge was actually associated with a pick outside the window.

The pixel selection and counting block 86 provides a count of pixels which occurred inside the window of valid picks. After the window opens, scan pick selection and counting 76 provides a short pulse on the gated pixels line 84 whenever the primary clock cycle is 25% complete. It should be noted that primary clock initiates new array pixels, therefore, counting clock cycles is synonymous with counting pixels. A clock counter in the pixel selection and counting block 86 increments whenever pulses are received on the gated pixels line 84. When a pick is detected inside the window by the scan pick selection and counting section 76, a short pulse is output on the pick detected line 85. If a pick is detected, the pulse on line 85 will occur 50% through the primary clock cycle. Pick pulses on line 85 cause the current state of the clock counter's output in 86 to be latched into an up/down counter inside 86. This process continues until the scan completes. At the end of a scan, the value latched into the up/down counter will be the number of pixels over which the counted pixels 300 lie. At the end of a scan, the up/down counter outputs its count serially to an incremental pixel counter inside 86 during a portion of the scan where the window will always be closed (129th through the 24th pixels).

When a read command is put out by timing control 52, the incremental density determination block 302 receives the summation of picks over k scans 300 and the summation of pixels over k scans 301 and computes the average incremental pick density $\rho_k$ over k scans per Eq. 1. Use of hardware incremental counters at the outputs of sections 76 and 86 ease the burden on the microcontroller which must perform the calculation of equation 1. In one embodiment, the number of scans k which are averaged by blocks 76 and 86 is set to 256. This configuration permits rapid scanning of the array without excessive burden on the microcontroller 32. After reading the count, the incremental density determination block 302 resets the incremental counters in blocks 76 and 86 in preparation for the next read cycle.

The incremental density value $\rho_k$ calculated by incremental density determination 302 corresponds to a small section of cloth (0.1" in the current embodiment). If pick density $\rho$ over longer sections of cloth are desired, consecutive incremental density values $\rho_k$ can be averaged as shown in block 90. In this embodiment, the user can select the number of determinations which are averaged in a traveling boxcar filter. Pick density accuracies on the order of 1% during a single scan can be obtained using 128 pixel arrays. Time and spatial averaging which occurs will significantly improve this accuracy and reduce signal noise. The accuracy can also be improved by using arrays with more pixels. Currently arrays are commercially available with at least 1024 pixels. The constant can be obtained by measuring the pick density of a grating or known cloth sample with the structure and yarn sensor. The resulting data set is averaged. It is advisable to move the calibration sample on the detector when collecting calibration data so the result contains both time and spatial averaging. The calibration constant is then selected to provide the correct response from the structure and yarn sensor to the known sample.

Pick Gradient

To detect rapid changes in pick density indicative of certain classes of defects (for example heavy start marks), a density gradient signal is useful. This density gradient is calculated in block 304 as the difference between consecutive incremental density values $\rho_k$.

Pick Count

It is also desirable to detect how many picks have been thrown by the loom. The incremental pick count, $c_k$, can be calculated using Eq. 2:

$$c_k = \sum_{i=1}^{k} c_p(i) \tag{2}$$

where k is the number of linear diode array scans collected by incremental counter 204 and $c_p(i)$ is the count of the fraction of a pick which has passed the structure and yarn sensor between the i−1th and i th scans. Incremental counter 204 outputs are accumulated by the pick accumulation and determination block 205. In addition, the pick accumulation and determination block 205 provides a preset function in response to a $l_{preset}$ input from the operator. The output from the pick accumulation and determination block 205 is the total pick count $c_p$ which is calculated as:

$$c_p = l_{preset} \cdot \rho^* + \sum_{j=1}^{m} c_p(j) \tag{3}$$

where $l_{preset}$ is a length preset provided by the user, $\rho^*$ is the next completely refreshed filtered density value after the preset, $c_p(j)$ is the jth output of the incremental pick counter 204, where j=1 at the first output of block 204 following the user preset, and where m is the most current output of block 204.

The embodiment which obtains the current pick count, $c_p$, is described below:

In some manufacturing applications, looms for example, the picks move in forward and reverse directions. The small reverse movement must be accounted for by the counting scheme to prevent errors in pick count. This embodiment develops quadrature signals from linear diode array data and uses a phase detector to develop direction sensitive counts of picks as the image passes a region near the center of the linear diode array 30.

The quadrature selection block 74 latches the discrete state of DO at two pixel locations near the center of the array. Pixels near the center of the array are used for obtaining quadrature signals since the illumination is best in this region. In the current embodiment, the 64 th and the 64+n th pixels are used. The user selectable integer n is chosen so that the two signals will be separated by approximately one-fourth of the typical distance between picks for the style of fabric being monitored. Thus, the outputs of quadrature selection, A and B, are discrete pulse trains having a quadrature relationship and are updated once each array scan. It is important that the scan rate of the linear diode array 30 be fast enough to assure that pick movement between scans does not approach one-quarter of a pick per scan.

A phase detector 78 receives the quadrature signals A and B. The initial phase detector embodiment uses these quadrature signals to generate four up pulses on 150 or down pulses on 151 for every pick which travels past the center region of the array in the forward or reverse direction, respectively. The factor of four introduced by the phase detector comes from the fact that the detector produces a pulse when either of the quadrature signals switch state. Alternative embodiments would produce either two pulses per pick or one pulse per pick. Another alternative embodiment is to use one direction line to indicate the forward or reverse direction and a second line to output pulses representative of pick movement. The current embodiment allows the user to change sign of the pick count to accommodate different orientations of the structure and yarn sensor on the process.

Incremental counter section 204 is used to count pulses from the phase detector which implements Eq. 2. The incremental counter architecture depends on what type of phase detector 78 is used. For the current embodiment, separate up and down counters are used to count pulses from lines 150 and 151. If a phase detector with direction and pulse outputs is used, a single counter can be employed which counts up or down depending on the state of the direction line. For the current embodiment, a pulse into incremental counter 204 represents either +0.25 or −0.25 of a pick depending on which line it was obtained from and the state of the user defined reverse signal. During many array scans, no pulse will be obtained.

The pick accumulation and determination block 205 accumulates counts $c_k$ stored in incremental counter 204 and provides necessary presets as required by the user. In the current embodiment, both the pick count $c_p$ and the fabric length $l_f$ are preset with the same preset command. Since the preset command has a length argument, the pick count is back calculated using the length argument and the next averaged measurement of pick density $\rho^*$. The assumption is made that the current measurement is an accurate representation of past density. Another embodiment would allow the operator to preset the count as well as the length.

Fabric Length

Fabric length $l_f$ is derived in the length accumulation and determination block 206 from the incremental pick count $c_k$ and the incremental pick density $\rho_k$ as:

$$l_f = l_{preset} + \sum_{j=1}^{m} \frac{c_p(j)}{\rho_k(j)} \quad (4)$$

where $l_{preset}$ is the length preset provided by the user, $c_k(j)$ is the jth output of the incremental pick counter 204, $\rho_k(j)$ is the jth output of incremental density determination 302, j=1 at the first output of blocks 302 and 204 after the preset, and j=m at the most current output from blocks 302 and 204. The preset provides users with a means of presetting the length of a roll to account for fabric manufactured before the structure and yarn sensor was brought on-line.

Fabric Velocity

Fabric velocity can also be calculated from $c_k$ and $\rho_k$ since the time over which the count was obtained is known. The fabric velocity is calculated in the velocity accumulation and determination block 207 as:

$$v_f = \sum_{j=1}^{l} \frac{c_k(j)}{\rho_k(j) \cdot 1 \cdot k \cdot t_s} \quad (5)$$

where 1 is the number of outputs of blocks 302 and 204 used in the calculation, k is the number of scans in the incremental determinations of $c_k$ and $\rho_k$, and $t_s$ is the scan time of each array cycle.

General Description

As mentioned above, the incremental counter 204 and the incremental counters in 76 and 86 rapidly collect scans so the microcontroller does not have to read counts each array scan. If necessary to accommodate fast moving fabric, these intermediate counters can be double buffered. In one embodiment, the incremental counter in 204 and the incremental counters in 76 and 86 collect 256 scans before being read for use by blocks 205, 206, 207 and 302. A read command is provided by the timing control 52 to signal the appropriate time to read the incremental counters. This read can be performed during the initial clock cycles of the array while the filters in blocks 60 and 62 are charging so that data is not lost. After reading the count, the incremental counters are reset in preparation for another series of scans.

In the discussion above, one embodiment is described which uses incremental counters to collect output from each array scan. For slow processes, it may be more appropriate to have the processor collect this information directly from the array. For faster applications, it may be appropriate to use a digital signal processor (DSP) to perform calculations of the microcontroller above. Another embodiment may perform all calculations in digital logic which would allow even faster applications to be accommodated. For embodiments using digital logic in the electronics 100 before the microcontroller, it is helpful to implement this functionality in a logic array to cut cost and size.

The light source in one embodiment is a Class 3a laser diode which was not collimated. For faster applications, brighter light sources can be used. The power can be decreased for slower applications. Alternate light sources include lasers, halogen lamps, light emitting diodes, and the like.

A control loop may be added in a preferred embodiment to adjust power to the light source 27 to maintain a near-maximum signal. This is accomplished by detecting the peak AO in a scan with a peak detector and adjusting power to the light source to maintain this peak at a desired level.

Interlocks have been provided in the current embodiment to remove power from the light source 27 when the cloth is not over the sensor window 202. This is accomplished by sensing when the output of the peak detector drops below a specified level. Additionally, the power to the light source 27 is removed if there are no picks detected by block 76 during a scan.

Use for Knitting

While the structure and yarn sensor implementation described above has been illustrated for a weaving application, the invention can also be used in knitting applications. When used on-line with a knitting machine, the preferred orientation is to configure the structure and yarn sensor to observe the course density which is analogous to pick density on a loom. This parameter is important because it is adjustable via tension on the machine. Equations which have been used to calculate pick density, pick density gradient, pick count, fabric length, and fabric velocity all apply to course density, course gradient, course count, fabric length and fabric velocity. Because of the geometry of a knitting machine, the structure and yarn sensor housing is aligned parallel with the wales. For courses to be monitored in this position, cylindrical lens 201 and linear diode array 30 must be rotated 90° about the axis of light propagation 48 from their positions shown in FIG. 2.

On-line inspection of the entire fabric requires an array capable of simultaneous inspection of as many courses as the machine has feeds. This is feasible using arrays having 512 or 1024 pixels which are commercially available. The rate at which the courses pass the detector is a few times faster than for typical loom applications. The increase in speed can be calculated by comparing the number of picks per minute produced by a loom to the number of knitting machine feeds times the knitting machine's rotations per minute.

Figure 5:
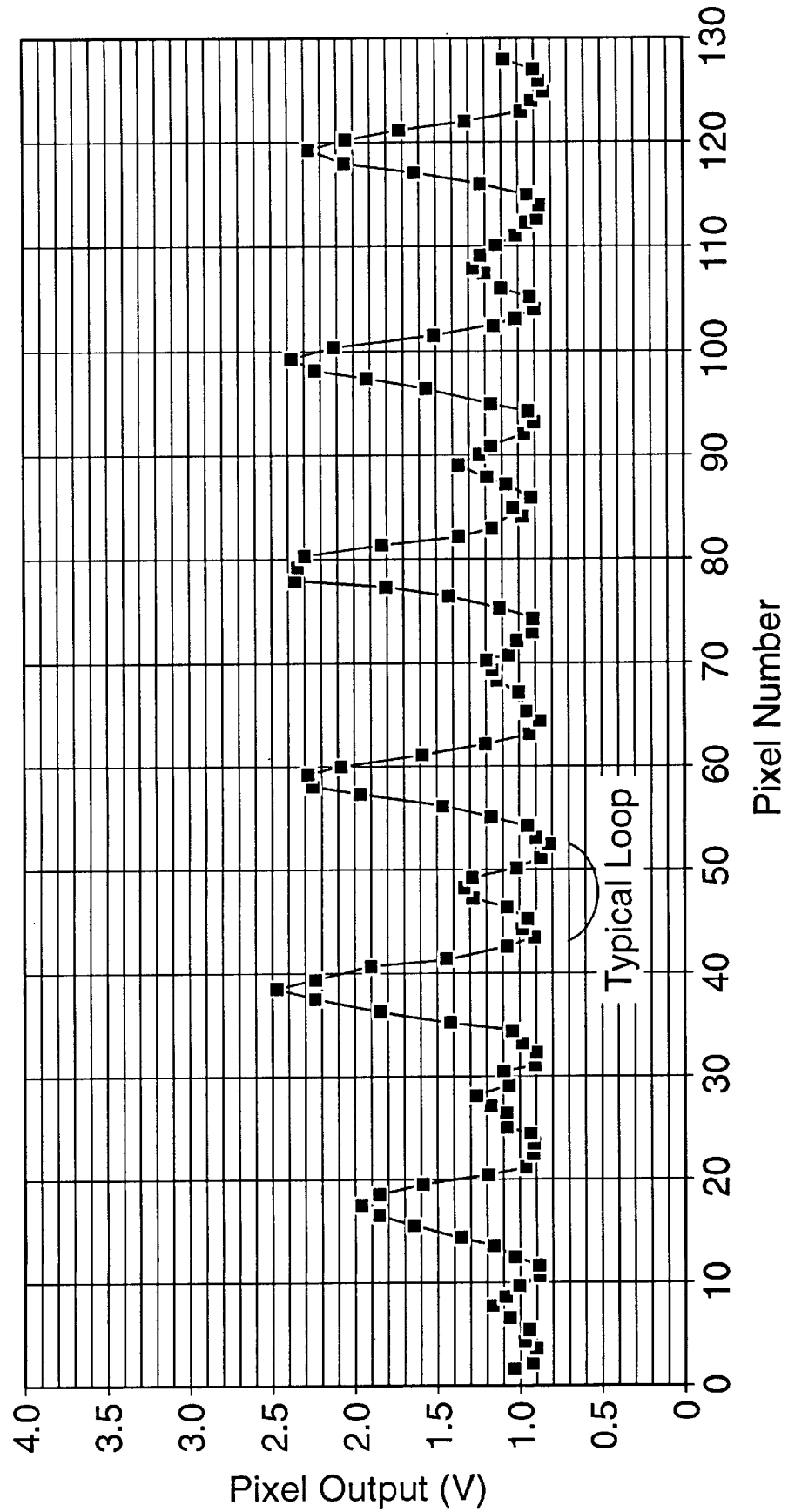
FIG. 5 is a plot of a scan of good knitted fabric showing several wales therein.

An alternative embodiment is also possible for on-line knitting machine applications where the structure and yarn sensor is configured to measure wales. Monitoring wales can prove useful in some fabric inspection applications. The orientation of the housing is identical to that described for knitting applications above. Cylindrical lens 201 and the linear diode array 30 are arranged as shown in FIG. 2. Since the wales come at higher velocities, it is necessary to provide a faster controller. FIG. 5 shows the output AO for back-lit fabric for a structure and yarn sensor configured to monitor wales. In FIG. 5, the short peaks are created by the center of the wale while the large peaks are generated by light passing around the outside of the wale. Since there are two peaks to every wale, the wale density and wale count is divided by two when using the equations for pick density presented earlier.

Off-line inspection of knitted fabric presents a slightly different situation. On a knitting machine, the fabric passes by the detector in a helix type pattern. After the fabric is knitted on a machine, the roll is removed for subsequent processing. When unrolled for processing, each course passes by a single point allowing the use of a low resolution detector similar to that used for the weaving application. The housing is oriented normal to fabric movement as shown in FIG. I and the lens arrangement of FIG. 2 is used. In this orientation, course density, course gradient, course count, fabric length, and fabric velocity may all be measured at the subsequent process using the equations presented for loom operation earlier. The response of AO when the structure and yarn detector is configured to measure courses will be shown in the next section.

Defect Detection

Two levels of defect detection are feasible using the structure and yarn sensor. First defect detection is possible by analyzing the AO signal and second by analyzing the pick density measurement. Basing algorithms on characteristics observed in the AO signal provides a more robust algorithm because the defect is not averaged with other good sections of fabric. However, the price tradeoff is that faster processing capability is necessary to collect and analyze data at the clock rates of the linear diode array.

Tests have been conducted where array scans were collected for various fabric defects. These defects for woven cloth included missed picks, double picks, and thin places (no picks are thrown over a region of fabric). This technique is also applicable to other full width defects in woven fabric.

Figure 6A:
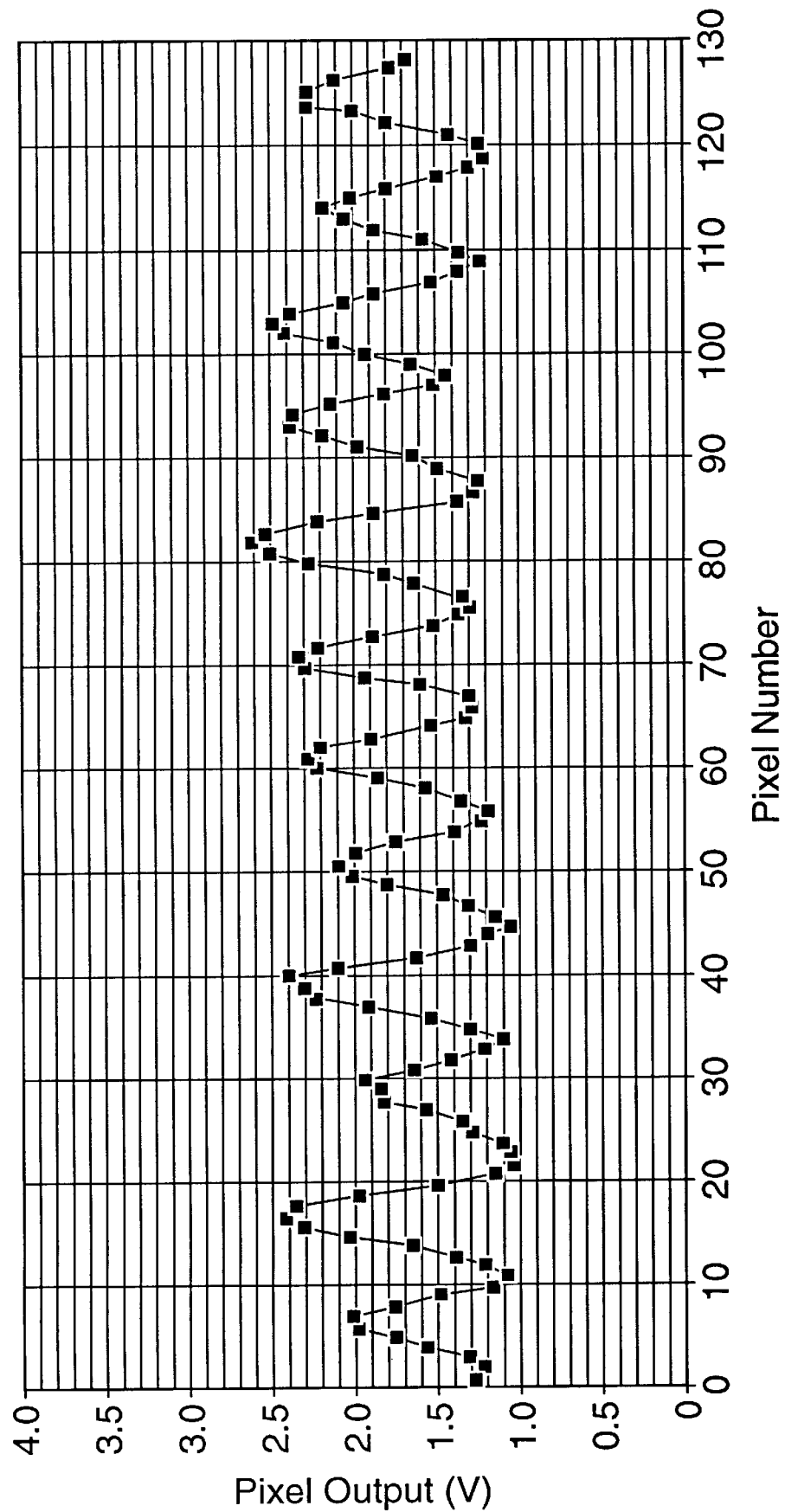
FIG. 6 contains plots of scans of woven fabric showing good fabric in part a and a a wide minimum caused by a missed pick therein in part b.
Figure 6B:
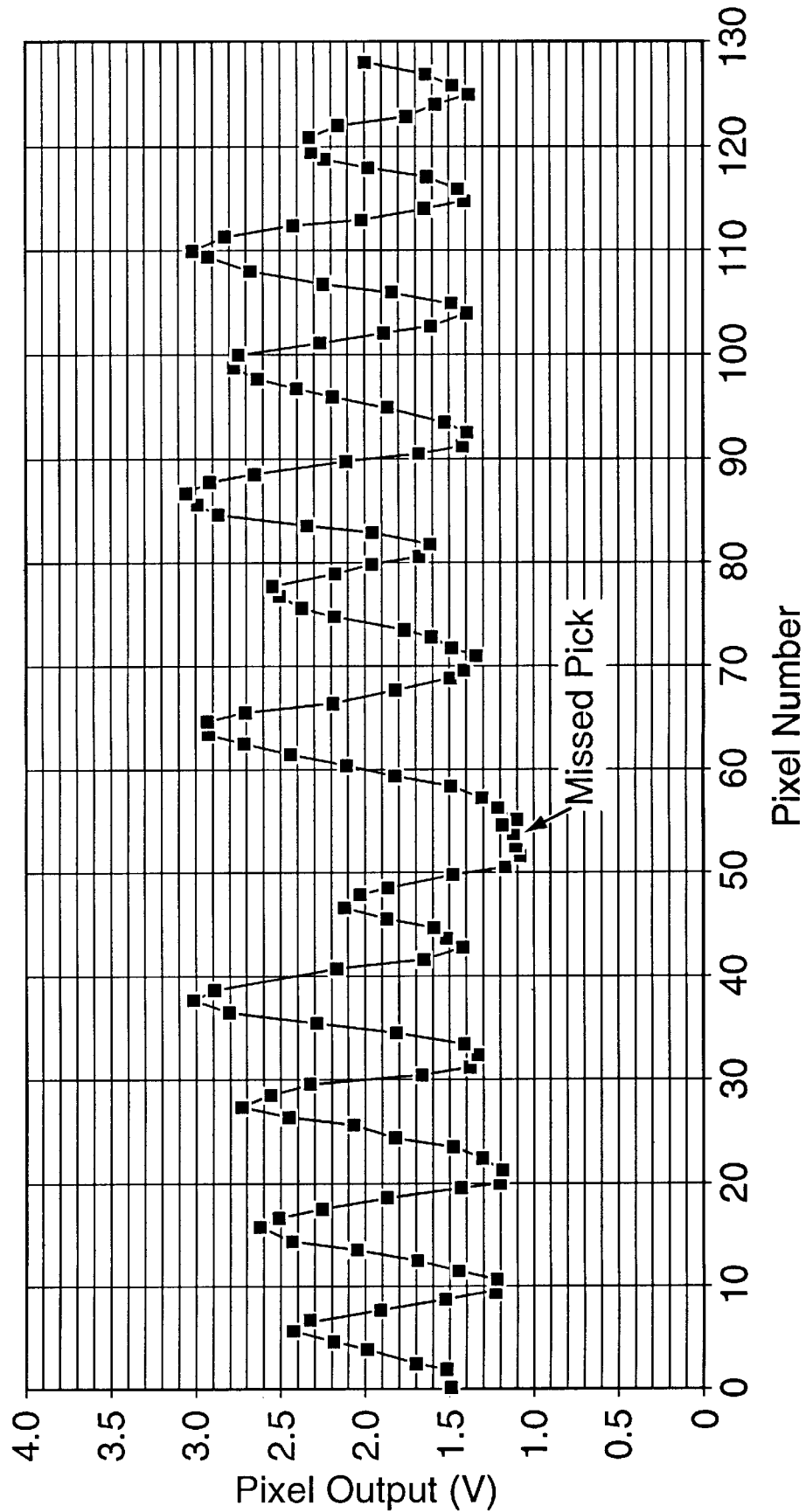

FIGS. 6a and 6b shows the linear diode array output AO for back-lit woven fabric. FIG. 6a is typical of output for good woven fabric which has a very periodic pick arrangement. FIG. 6b contains the output for woven fabric with a missed pick. When a pick is missed, the adjacent picks are forced together forming what appears to be a very wide pick. For back-lit cloth, this appears as a wide minima. This minima is located around pixel 54th pixel in the scan of the lower portion of FIG. 6. By measuring the width of picks as the distance between maxima (gaps in fabric for back-lit case), missed picks are on the order of 45% to 70% wider than good fabric. Similarly, double picks which also cause two picks to be forced together have a pick width on the order of 25% wider than good cloth. Thin places are easily detected as a continuous maxima with no dips.

Figure 8:
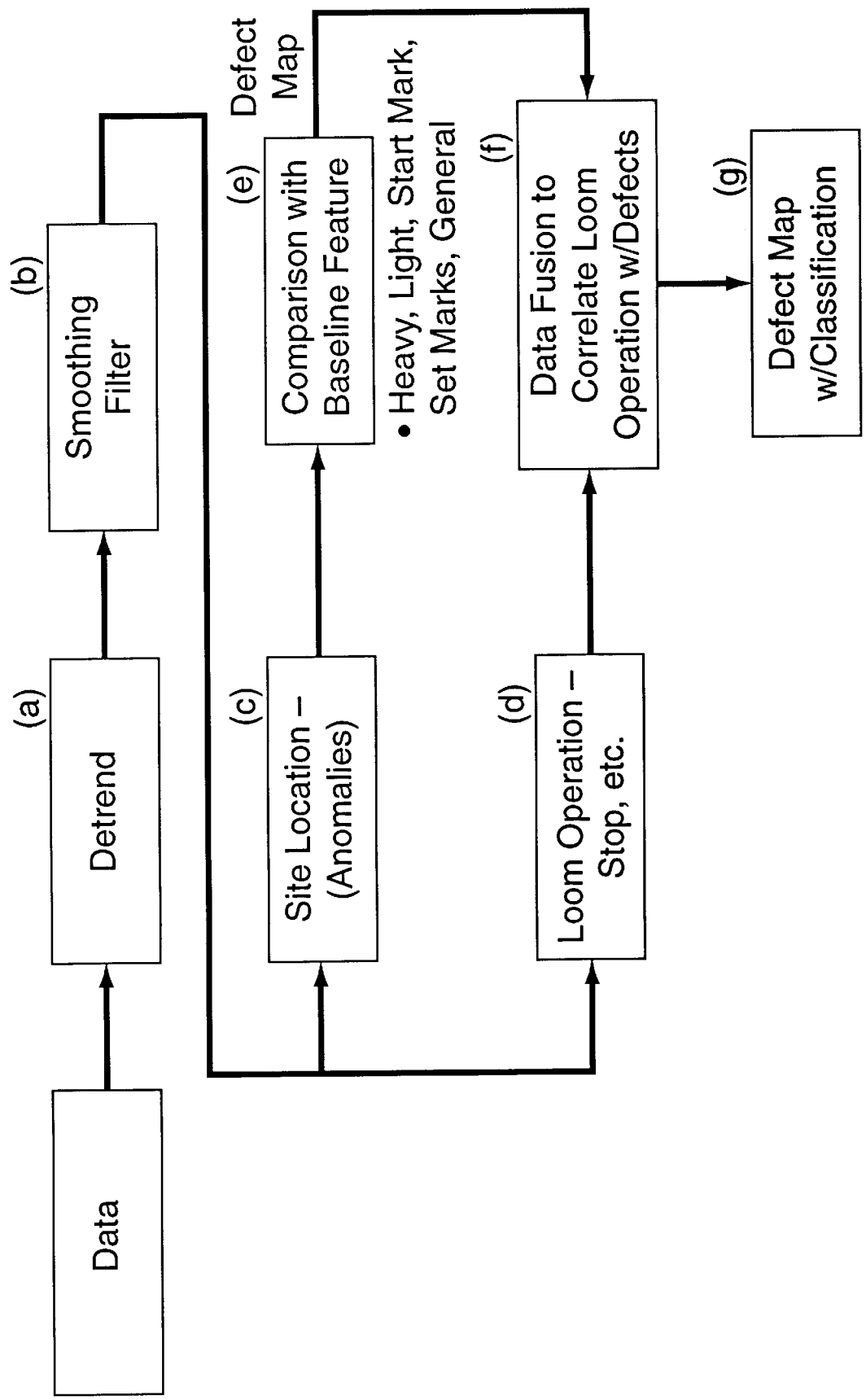
FIG. 8 is a block diagram of an algorithm for comparing the pick density measurement to a base-line signature obtained from normal or good cloth.
Figure 9:
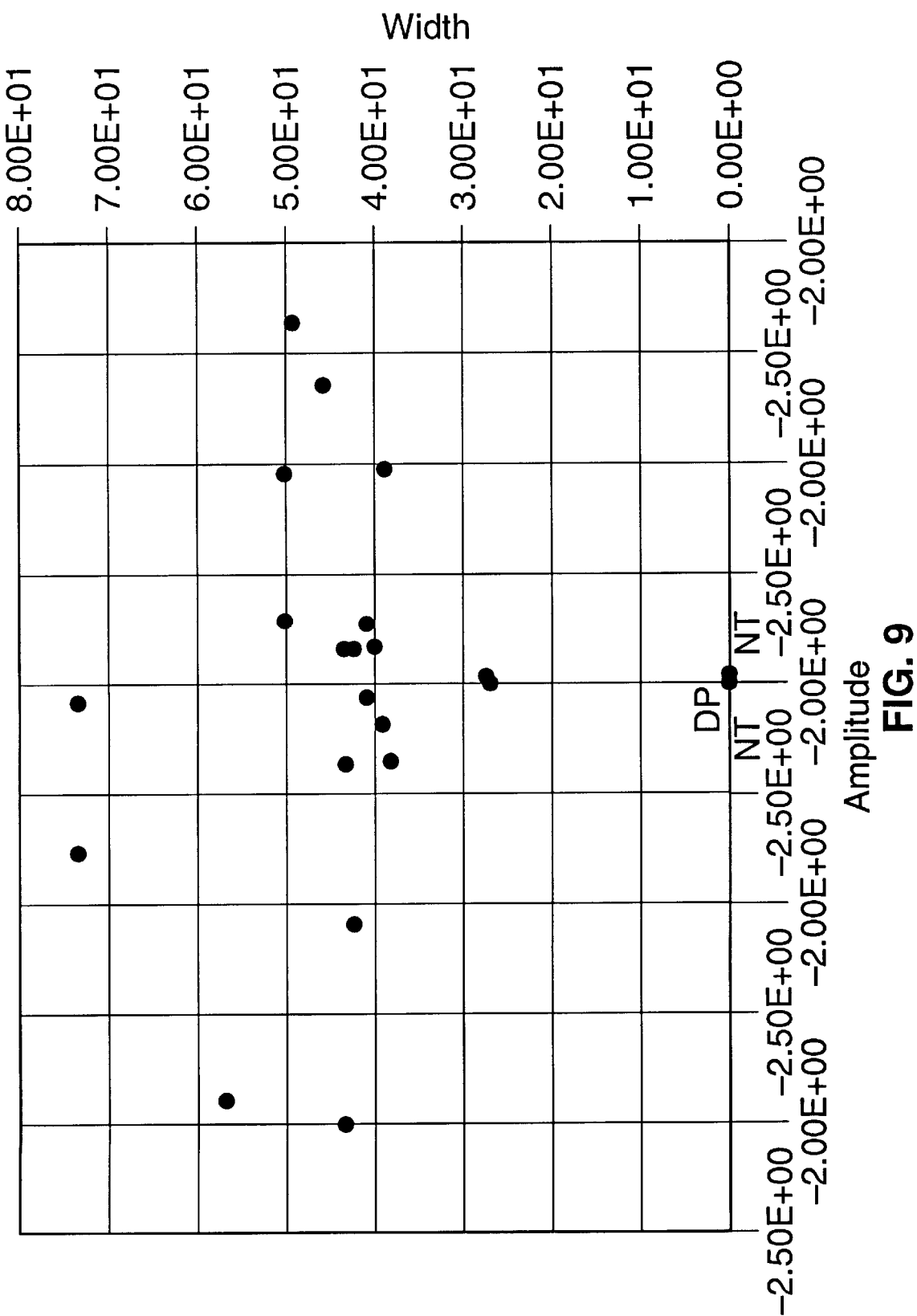
FIG. 9 is a plot of the features associated with 23 defects and their site locations.

The second method is based on analyzing the pick density measurement and comparing this to a base-line signature obtained from normal or good cloth. FIG. 8 shows a block diagram of the algorithm identifying the seven elements associated with it. As shown, the data is detrended (a) and processed with a smoothing filter (b) before being handed to the two concurrent tasks of locating potential defect sites or anomalies (c) and analyzing the loom operational parameters (d). At this point, the site location information is passed to task (e) where the features of each site are compared with those of known defects. FIG. 9 is a plot of the features (amplitude and pulse width) associated with 23 site locations. Each is labeled if its features correlate with a known defect. This data is then passed to task (f) where the defects and loom stops are correlated for further classification. At this point the defects are identified as set marks, stop marks, and loom stops. Once this is completed, a defect map, FIG. 10, is generated describing defects, locations, and classifications.

Defects in knitted fabric are also detectable using the structure and yarn sensor. Defects in knitted goods which have been tested include thin yarn, heavy yarn, holes, drop stitches, and needle runs, however, the device may be used to detect and map other knitting defects (slubs, double yarn, and the like). All these defects have distinguishing characteristics as compared to good fabric.

Figure 7A:
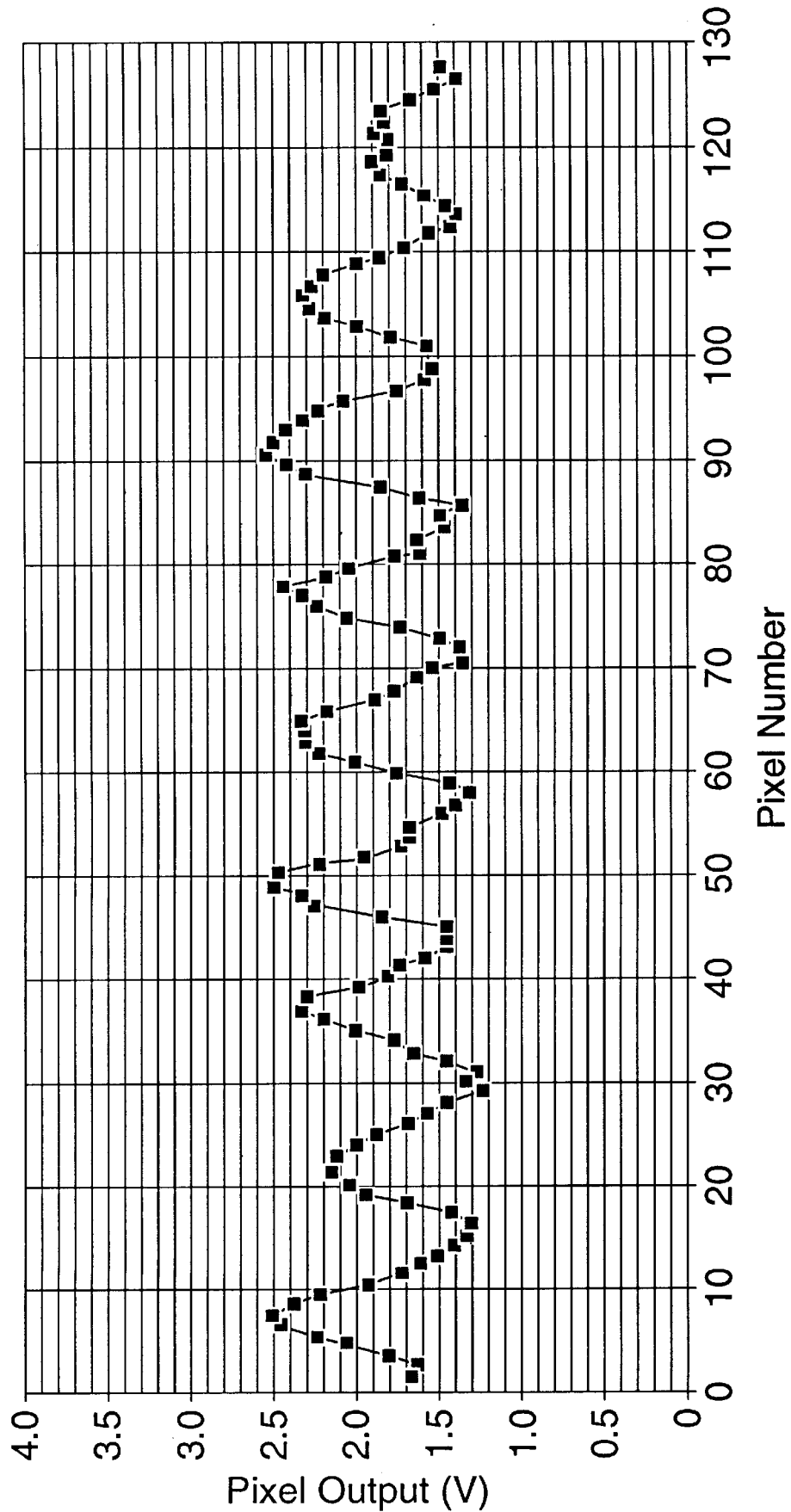
FIG. 7 contains plots of a scan of knitted fabric oriented to monitor courses with part a showing good fabric and part b showing the effect of thin yarn therein.
Figure 7B:
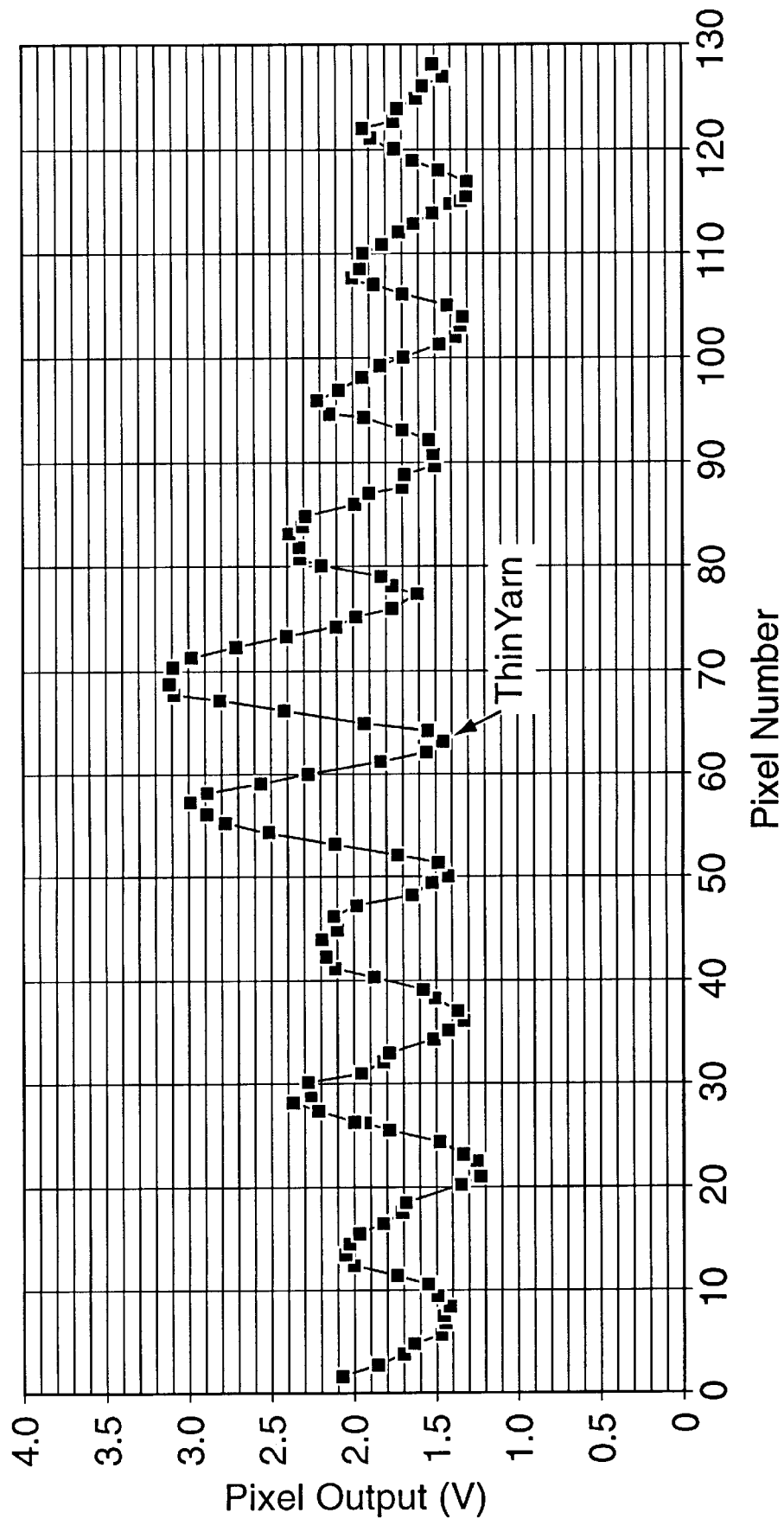

FIGS. 7a and 7b show the linear diode array output AO for back-lit knitted fabric. FIG. 7a shows AO output typical of good knitted fabric. The sensor is oriented so that courses are shown. Since the fabric is back-lit, presence of yarn creates a minima on the detector's output. FIG. 7b shows linear diode array output for fabric with thin yarn at one feed. The most distinctive feature about thin yarn is the pair of high maxima created by thin yarn. Peaks caused by excessive void space on either side of the thin yarn are located at pixels 57 and 69 in FIG. 7b.

Other defects also produce distinctive structure when compared to good cloth. Thick yarn exhibits a pair of very low maxima on either side of the thick yarn for back-lit fabric. Holes, drop stitches, and needle runs appear as very high and wide peaks when the structure and yarn sensor is configured to measure in the warp direction. These defects often saturate the AO signal. Widths of these peaks are at least two times as wide as a normal maxima in good cloth. Needle runs are distinguished from holes or drop stitches because loops adjacent to the defect appear normal. Because of the large voids in holes, drop stitches, and needle runs, they are also detected with the structure and yarn sensor configured to measure in the course direction. Holes, drop stitches, and needle runs are distinguished from thin yarn by the saturation of the signal.

The examples given in the defect detection section have include both front and back lighting. Front lit fabric also produces good fabric defect detection results, however maxima and minima are reversed. It is important to assure that the fabric is evenly illuminated when doing defect detection using the AO output. An alternative to even illumination is to correct for biases in illumination with the processor which provides the defect analysis. Two schemes for defect detection have been described. Both methods can be applied to either woven or knitted fabric.

Patterns

Figure 11:
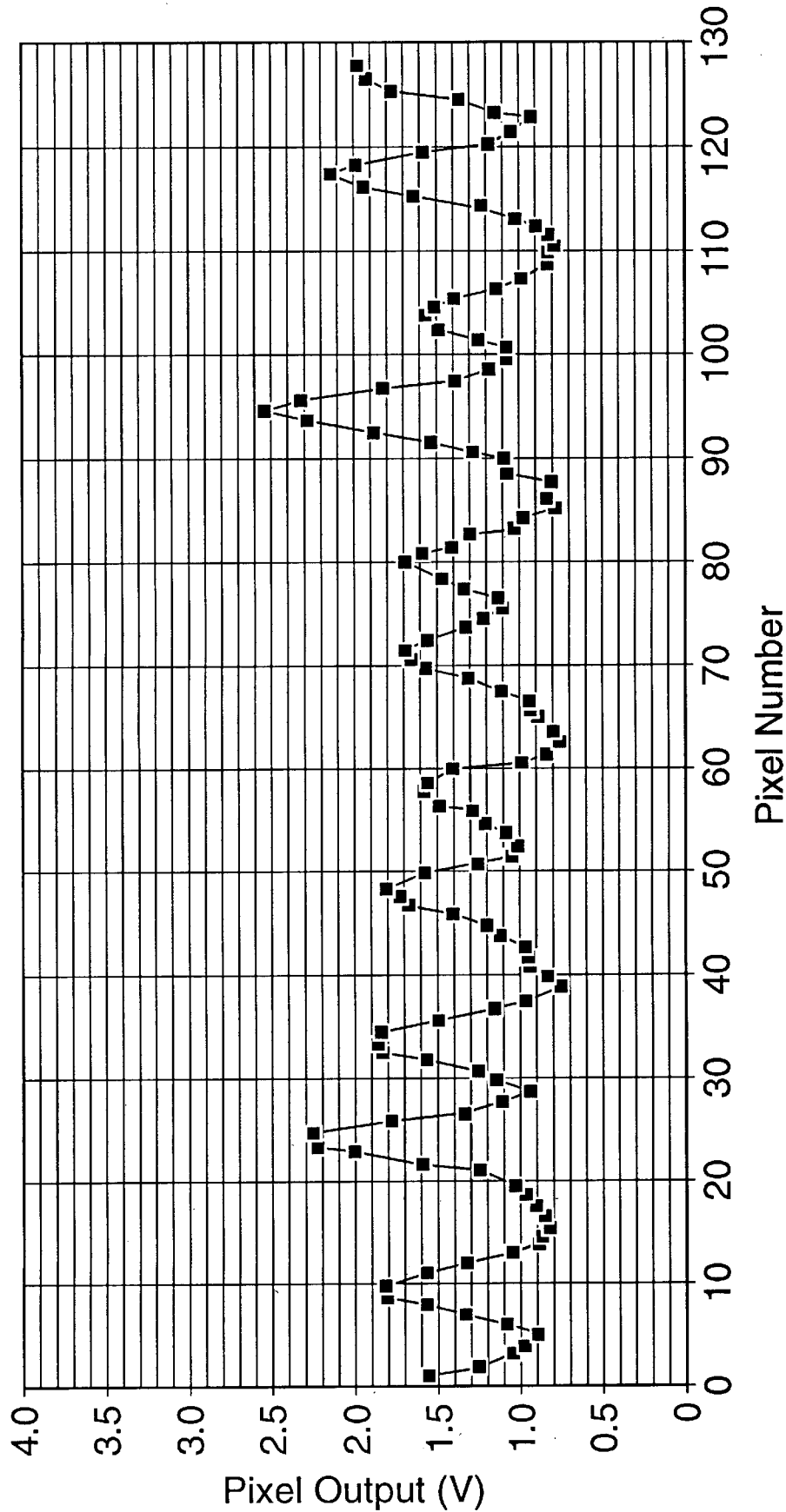
FIG. 11 is a plot of a scan of woven fabric showing a one-pick two-pick pattern therein.

A natural extension of detection of double yarn is the detection of patterns in fabric. Often these patterns in woven fabric are obtained by filling (inserting picks) with a pair of picks. The same techniques used above for detection of defects apply to the detection of patterns. FIG. 11 shows the output AO for back-lit fabric from a loom where double and single picks were alternatively inserted. By measuring the distance between maxima (i.e. spaces between picks), a roughly 45% increase in width on every other pick is clearly detectable. This technique is valuable for detecting defects in the intended pattern or for verifying that the pattern was set up properly on the loom.

Concluding Comments

The structure and yarn sensor apparatus is compact so that it can be used in tight spots on looms, on knitting machines, near take-up rolls, or on various other processes. The device can be used in on-line as well as off-line applications. From the foregoing, it will be appreciated that the structure and yarn sensor apparatus according to the invention directly detects pick and course density, pick and course density gradient, pick and course count, fabric length and fabric velocity. Additionally, full width defects on a loom and defects on knitted cloth can be detected. The structure and yarn sensor can also be used for verification of patterns in fabrics.

While the loom application allowed use of a low power laser diode (Class 3a) and inexpensive microcontrollers, use of higher power light sources and faster processors enable faster applications.

While particular forms of the invention have been illustrated and described, it will be apparent that various modifications can be made without departing from the spirit and scope of the invention.

We claim:

1. A structure and yarn sensor apparatus for use with a fabric made with a plurality of yarns moving in a direction of travel, the fabric having a front side and a back side, the yarns being disposed generally across the width of the fabric, comprising:

(A) a light source directed so that light impinges upon a side of the fabric in a path of light propagation;

(B) a focusing lens disposed in the path of light propagation to focus the light;

(C) an astigmatic lens disposed in the path of light propagation to allow selective imaging of yarn in one dimension to be imaged on an array;

(D) an array comprising photodetectors, the array having a face, the photodetectors being disposed so that the focused light from the focusing lens impinges upon the face of the array of photodetectors to produce a scan, wherein the face is divided into a multiplicity of pixels, the array of photodetectors producing an output signal based on the fabric moving in the direction of travel during the scan;

(E) a timing control means producing a velocity gate signal, clock signals, a read signal, and a scan start signal, wherein the clock signal and the scan start signal are coupled to the array of photodetectors;

(F) a smoothing filter means coupled to the output of the array of photodetectors;

(G) a bias detection means coupled to the output of the array of photodetectors;

(H) a discriminator means having a positive input and a negative input, wherein one input is coupled to the output of the smoothing filter means and the other input is coupled to the output of the bias detection means;

(I) a pick selection and counting means having an input port, a reset port, and clock signal input ports, wherein the input port is coupled to the output of the discriminator port, the reset port is coupled to the scan start signal, and the clock inputs are coupled to the timing control clock signals, and wherein the scan pick selection and counting means determines which picks imaged on the face of the photodetectors during a scan will be used in the density calculation, provides a gated pixels signal during a scan while picks are being counted, provides a pick detected signal during a scan each time an additional pick is counted, and outputs a collected count of picks over multiple scans;

(J) a pixel selection and counting means having a reset port, an input port, clock signal input ports, and a pick detected input port, wherein the reset port is coupled to the scan start signal, the input port is coupled to the gated pixels signal, the clock inputs are coupled to the timing control clock signals, and the pick detected import port is coupled to the pick detected output, and wherein the pixel selection and counting means counts pixels during scans corresponding to the count of picks and outputs a collected count of pixels over multiple scans;

(K) an incremental pick density determination means having inputs coupled to the read signal, the scan pick selection and counting output and the pixel selection and counting output, wherein the pick density calculation means produces an incremental pick density signal based on the pick count and the pixel count, wherein the pick density signal is representative of the density of picks in the fabric object imaged on the face of the array of photodetectors, and wherein the incremental pick density processor means resets scan pick selection and counting and pixel selection and counting means after performing a read.

2. An apparatus as described in claim 1, further comprising:

(L) a quadrature selection means coupled to the output of the discriminator means, wherein the quadrature selection means produces quadrature outputs means based on the discriminator output during selected pixels; and (M) a phase detector means coupled to the output of the quadrature selection means, wherein the phase detector means produces, based on quadrature signals, one or more pulses for each pick in the fabric imaged on the face of the array which passes a center region of the array, including information on the direction of movement; and (N) an incremental counter means having a pair of inputs from the phase detector wherein an output is provided representing the count of pixels during a selected number of scans.

3. An apparatus as described in claim 2, further comprising:

(O) a pick accumulation and determination means coupled to the incremental counter and having a read input and a user preset input, which provides an accumulated output of the incremental pick counts with the capability of presetting the output based on a user preset input and which resets the incremental counter after reading its count; and (P) a fabric length accumulation and determination means having a preset port and a read port and being coupled to the incremental density output and the incremental counter output, wherein the fabric length accumulation and determination means produces, based on its inputs, a fabric length signal representative of the length of the fabric.

4. An apparatus as described in claim 2, further comprising:

(Q) a fabric velocity calculation means having a read port and a velocity gate port coupled to the average density output and the incremental counter output, wherein the fabric velocity calculation processor produces, based on its inputs, a fabric velocity signal representative of the velocity of the fabric.

5. An apparatus as described in claim 1, wherein the array of photodetectors comprises a linear array.

6. An apparatus as described in claim 1, wherein each element of the array of photodetectors comprises a photodiode.

7. An apparatus as described in claim 1, wherein the focusing lens comprises a nonastigmatic lens and an astigmatic lens.

8. An apparatus as described in claim 1, wherein the focusing lens comprises a cylindrical convex lens.

9. An apparatus as described in claim 1, wherein light from the light source impinges upon the side of the fabric opposite the array of photodetectors.

10. An apparatus as described in claim 1 wherein light from the light source impinges upon the fabric from the same side as the array of photodetectors.

11. An apparatus as described in claim 1 wherein light from the light source is generated by means selected from the group of means consisting of laser diodes, lasers, halogen lamps, and light emitting diodes.

12. A method for determining a yarn density in a fabric made with a plurality of yarns, the fabric having a front side and a back side, and having yarns which are disposed generally across the width of the fabric, comprising the steps of:

(A) moving the fabric in a direction of travel, (B) directing a light source so that light impinges upon the fabric in a path of light propagation;

(C) focusing the light so that the light impinges upon an array of photodetectors, wherein the array of photodetectors has a face which is divided into a multiplicity of pixels, wherein a number of yarns in a single direction in the fabric is imaged on a number of pixels in the face of the array of photodetectors to produce a scan;

(D) operating the array of photodetectors during a scan to produce an output signal which is based on the fabric moving in the direction of travel during the scan;

(E) counting the number of selected yarns in the fabric imaged on the face of the array of photodetectors during the scan;

(F) counting the number of pixels in the face of the array of photodetectors on which the number of selected yarns in the fabric is imaged during the scan; and (G) determining the yarn density based on the number of yarns and the number of pixels.

13. A method as described in claim 12, wherein the array of photodetectors comprises a linear array.

14. A method as described in claim 12, wherein each element of the array of photodetectors comprises a photodiode.

15. A method as described in claim 12, wherein the step of focusing the light is accomplished by utilizing at least one nonastigmatic lens and at least one astigmatic lens.

16. A method as described in claim 12, wherein the step of focusing the light is accomplished by utilizing at least one astigmatic lens.

17. A method as described in claim 12, wherein light from the light source impinges upon the side of the fabric opposite the array of photodetectors.

18. A method as described in claim 12, wherein light from the light source impinges upon the fabric from the same side as the array of photodetectors.

19. A method as described in claim 12 wherein light from the light source is generated by means selected from the group of means consisting of laser diodes, lasers, halogen lamps, and light emitting diodes.

20. A method for detecting defects and patterns in a fabric made with a plurality of yarns, the fabric having a front side and a back side, the method comprising the steps of:

(A) moving the fabric in a direction of travel;

(B) directing a light source so that light impinges upon the fabric in a path of light propagation;

(C) focusing the light so that the light impinges upon an array of photodetectors to produce an image upon the array of photodetectors, the image appearing as a set of parallel lines, each line representing one yarn in the fabric, wherein the array of photodetectors has a face which is divided into a multiplicity of pixels, wherein a number of yarns in a single direction in the fabric are imaged on a number of pixels in the face of the array of photodetectors to produce a scan;

(D) operating the array of photodetectors during a scan to produce an output signal based on the fabric moving in the direction of travel during the scan;

(E) obtaining a signal, based on the output signal from the array of photodetectors; and (F) determining any characteristic selected from the group consisting of defects and patterns in the fabric based on the signal from the array of photodetectors.

21. A method as described in claim 20, wherein the array of photodetectors comprises a linear array.

22. A method as described in claim 20, wherein each of the array of photodetectors comprises a photodiode.

23. A method as described in claim 20, wherein the step of focusing the light is accomplished by utilizing a pair of plano-convex lenses.

24. A method as described in claim 20, wherein the step of focusing the light is accomplished by utilizing at least one nonastigmatic lens and at least one astigmatic lens.

25. A method as described in claim 20, wherein the step of focusing the light is accomplished by utilizing at least one astigmatic lens.

26. A method as described in claim 20, wherein light from the light source impinges upon the side of the fabric opposite the array of photodetectors.

27. A method as described in claim 20 wherein light from the light source impinges upon the fabric from the same side as the array of photodetectors.

28. A method as described in claim 20 wherein light from the light source is generated by means selected from the group of means consisting of laser diodes, lasers, halogen lamps, and light emitting diodes.

29. A method for determining at least one parameter selected from the group consisting of fabric length and fabric velocity in a fabric made with a plurality of yarns during a period of elapsed time, the fabric having a front side and a back side, the method comprising the steps of:

(A) moving the fabric in a direction of travel;

(B) directing a light source so that light impinges upon the fabric in a path of light propagation;

(C) focusing the light so that the light impinges upon an array of photodetectors to produce an image upon the array of photodetectors, the image appearing as a set of parallel lines, each line representing one yarn in the fabric, wherein the array of photodetectors has a face which is divided into a multiplicity of pixels, wherein a number of yarns in a single direction in the fabric are imaged on a number of pixels in the face of the array of photodetectors to produce a scan;

(D) operating the array of photodetectors during a scan to produce an output signal based on the fabric moving in the direction of travel during the scan;

(E) counting yarns in the fabric imaged on the face of the array of photodetectors as they pass at least one pixel to determine yarn count;

(F) counting the number of selected yarns in the fabric imaged on the face of the array of photodetectors during the scan;

(G) counting the number of pixels in the face of the array of photodetectors on which the number of selected yarns in the fabric is imaged during the scan;

(H) determining the yarn density based on the number of yarns and the number of pixels and (I) determining said at least one parameter selected from the group consisting of fabric length and fabric velocity based on at least two of the group consisting of yarn count, yarn density, and elapsed time.

30. A method as described in claim 29 wherein the array of photodetectors comprises a linear array.

31. A method as described in claim 29, wherein each photodetector comprises a photodiode.

32. A method as described in claim 29 wherein the step of focusing the light is accomplished by utilizing a pair of plano-convex lenses.

33. A method as described in claim 29 wherein the step of focusing the light is accomplished by utilizing at least one nonastigmatic lens and at least one astigmatic lens.

34. A method as described in claim 29 wherein the step of focusing the light is accomplished by utilizing at least one astigmatic lens.

35. A method as described in claim 29 wherein the light from the light source impinges upon the fabric opposite the array of photodetectors.

36. A method as described in claim 29 wherein the light from the light source impinges upon the fabric from the same side as the array of photodetectors.

37. A method as described in claim 29 wherein light from the light source is generated by means selected from the group of means consisting of laser diodes, lasers, halogen lamps, and light emitting diodes.

38. A method for determining yarn count in a fabric made with a plurality of yarns during a period of elapsed time, the fabric having a front side and a back side, the method comprising the steps of:

(A) moving the fabric in a direction of travel;

(B) directing a light source so that light impinges upon the fabric in a path of light propagation;

(C) focusing the light so that the light impinges upon at least one photodetector to produce an image, the image appearing as a set of parallel lines, each line representing one yarn in the fabric;

(D) operating the at least one photodetector to produce an output signal based on the fabric moving in the direction of travel; and (E) counting yarns in the fabric imaged on the at least one photodetector as the image passes the at least one photodetector during the period of elapsed time to determine yarn count.

39. A method as described in claim 38, wherein each at least one photodetector comprises a photodiode.

40. A method as described in claim 38 wherein the step of focusing the light is accomplished by utilizing a pair of plano-convex lenses.

41. A method as described in claim 38 wherein the step of focusing the light is accomplished by utilizing at least one nonastigmatic lens and at least one astigmatic lens.

42. A method as described in claim 38 wherein the step of focusing the light is accomplished by utilizing at least one astigmatic lens.

43. A method as described in claim 38 wherein the light from the light source impinges upon the fabric opposite the at least one photodetector.

44. A method as described in claim 38 wherein the light from the light source impinges upon the fabric from the same side as the at least one photodetector.

45. A method as described in claim 38 wherein light from the light source is generated by means selected from the group of means consisting of laser diodes, lasers, halogen lamps, and light emitting diodes.

* * * * *